(12) United States Patent
Mimura et al.

(10) Patent No.: US 7,476,768 B2
(45) Date of Patent: Jan. 13, 2009

(54) CATALYST FOR OXIDIZING 2,2,2-TRIFLUOROETHANOL AND PROCESS FOR PRODUCING TRIFLUOROACETALDEHYDE

(75) Inventors: Hideyuki Mimura, Shunan (JP); Akio Watanabe, Shunan (JP); Noritaka Nagasaki, Hofu (JP); Kosuke Kawada, Kudamatsu (JP)

(73) Assignee: Tosoh F-Tech, Inc., Yamaguchi (JP)

( * ) Notice: Subject to any disclaimer, the term of this patent is extended or adjusted under 35 U.S.C. 154(b) by 0 days.

(21) Appl. No.: 11/792,255

(22) PCT Filed: Nov. 29, 2005

(86) PCT No.: PCT/JP2005/021834

§ 371 (c)(1),
(2), (4) Date: Jul. 6, 2007

(87) PCT Pub. No.: WO2006/062003

PCT Pub. Date: Jun. 15, 2006

(65) Prior Publication Data

US 2008/0132727 A1    Jun. 5, 2008

(30) Foreign Application Priority Data

Dec. 10, 2004    (JP)    ............ 2004-357499

(51) Int. Cl.
*C07C 45/29*    (2006.01)
(52) U.S. Cl. ...................................... 568/470
(58) Field of Classification Search ................ 502/308, 502/310, 349; 568/470
See application file for complete search history.

(56) References Cited

U.S. PATENT DOCUMENTS

| 3,038,936 A | * | 6/1962 | Braid et al. ................. 562/538 |
| 5,877,330 A | | 3/1999 | Kishimoto et al. |
| 6,281,378 B1 | | 8/2001 | Kishimoto et al. |
| 2003/0166972 A1 | | 9/2003 | Liu et al. |
| 2004/0044252 A1 | | 3/2004 | Liu et al. |

FOREIGN PATENT DOCUMENTS

| EP | 0 603 409 | 6/1994 |
| EP | 0 775 519 | 5/1997 |
| JP | 2005-517727 | 6/2005 |
| WO | 93/25308 | 12/1993 |
| WO | 96/41678 | 12/1996 |
| WO | 03/070668 | 8/2003 |

* cited by examiner

*Primary Examiner*—Sikarl A Witherspoon
(74) *Attorney, Agent, or Firm*—Wenderoth, Lind and Ponack, L.L.P.

(57) ABSTRACT

A catalyst for oxidizing 2,2,2-trifluoroethanol to form trifluoroacetaldehyde. The catalyst has a long life and achieves high conversion and selectivity.

The catalyst of the present invention comprises one or more metal oxides, including at least vanadium oxide, and zirconia as a carrier.

6 Claims, No Drawings

US 7,476,768 B2

CATALYST FOR OXIDIZING 2,2,2-TRIFLUOROETHANOL AND PROCESS FOR PRODUCING TRIFLUOROACETALDEHYDE

TECHNICAL FIELD

The present invention relates to a catalyst for producing trifluoroacetaldehyde and a process for producing trifluoroacetaldehyde using the catalyst.

More particularly, the present invention relates to a catalyst that can oxidize 2,2,2-trifluoroethanol with molecular oxygen or a molecular oxygen-containing gas in a gas-phase oxidation process to produce trifluoroacetaldehyde and/or a trifluoroacetaldehyde hydrate. The present invention further relates to a process for producing trifluoroacetaldehyde and/or a trifluoroacetaldehyde hydrate using such a catalyst.

BACKGROUND ART

Trifluoroacetaldehyde can be stably stored as a trifluoroacetaldehyde hydrate or a trifluoroacetaldehyde hemiacetal, which can be converted to various trifluoromethyl compounds either directly or, if necessary, after dehydration or dealcoholization. Thus, the compound is highly useful an intermediate to make pharmaceutical and agrochemical products and electronic materials.

Among known processes for the synthesis of trifluoroacetaldehyde are:

(1) hydrolysis of trifluorochlorobromoethane (See, for example, Patent Document 1);

(2) fluorination of trichloroacetaldehyde in the gas phase reaction (See, for example, Patent Document 2);

(3) reduction of trifluoroacetic acid or trifluoroacetate in the liquid or solid phase (See, for example, Non-Patent Document 1 and Patent Document 3); and (4) gas phase oxidation of trifluoroethanol (Patent Document 4).

Each process has its own drawbacks as follows. The process (1) involves the use of toxic mercury compounds. The process (2) requires complex procedures to remove incompletely fluorinated by-products with unsubstituted chlorine atoms. The process (3) as described in Non-Patent Document 1 involves the use of extremely flammable metal hydrides. The same process as described in Patent Document 3 results in an insufficient conversion, so that unreacted trifluoroacetic acid must be collected. In this instance, the products of trifluoroacetaldehyde and trifluoroacetic acid both form azeotropic mixtures with water (having bps of 106° C. and 105.5° C., respectively). Therefore, the separation process is complicated.

The process (4) is relatively simple since the process does not give inseparable by-products and since unreacted 2,2,2-trifluoroethanol can be readily separated by distillation. In Patent Document 4, trifluoroacetaldehyde is obtained at a high selectivity by subjecting 2,2,2-trifluoroethanol to gas-phase oxidation using as a catalyst a metal oxide selected from the group consisting of vanadium, chromium, molybdenum, tungsten and uranium. However, the process can achieve only a low conversion and, thus, low productivity. A process described in Patent Document 5 manages to improve the conversion by using a $0.1TiO_2$-$0.9V_2O_5$ catalyst along with an air-ozone mixture serving as a raw material gas, and carrying out the reaction at 390 to 420° C. Nevertheless, trifluoroacetaldehyde cannot be achieved at 100% selectivity even by the use of this catalyst. Thus, hydrogen fluoride, a highly corrosive by-product resulting from this combustion process, reduces the life of the catalyst and makes it difficult to achieve good results for an extended period of time. Although the reduced catalyst life is the most important drawback of the production of trifluoroacetaldehyde by the oxidation of 2,2,2-trifluoroethanol, the above-described Patent Document fails to provide any effective solution to the problem.

Patent Document 1 Czechoslovakia Patent No. 136870

Patent Document 2 Japanese Patent Publication No. Sho 63-15254

Patent Document 3 Japanese Patent Laid-Open Publication No. Hei

Patent Document 4 U.S. Pat. No. 3,038,936

Patent Document 5 Soviet Union Patent No. 1715799

Non-Patent Document 1 J. Am. Chem. Soc., 76, 300 (1954)

DISCLOSURE OF THE INVENTION

Problems to be Solved by the Invention

The present invention has been devised for the purpose of providing effective solutions to the above-described problems. Accordingly, it is an object of the present invention to provide a catalyst that can convert 2,2,2-trifluoroethanol into trifluoroacetaldehyde at high conversion and high selectivity and that has a long life. It is another object of the present invention to provide a process for producing trifluoroacetaldehyde and/or a trifluoroacetaldehyde hydrate using the catalyst.

Means for Solving the Problems

In the course of our study to achieve the above-described objects, the present inventors have found that the conversion of 2,2,2-trifluoroethanol into trifluoroacetaldehyde largely depends on the type of the catalyst carrier used and by using a catalyst composed of a particular carrier and at least one metal oxide including vanadium oxide, trifluoroacetaldehyde can be produced at high conversion and high selectivity. The present inventors have also found that such a catalyst maintains its catalytic activity for an extended period of time and can be used to effectively produce trifluoroacetaldehyde. These discoveries ultimately led to the present invention. Specifically, the present invention concerns the following aspects:

(1) A catalyst for oxidation of 2,2,2-trifluoroethanol, comprising one or more metal oxides, including at least vanadium oxide, and zirconia as a carrier.

(2) The catalyst for oxidation of 2,2,2-trifluoroethanol according to (1) above, wherein zirconia has a specific surface area in the range of 10 to 200 $m^2/g$.

(3) The catalyst for oxidation of 2,2,2-trifluoroethanol according to (1) or (2) above, wherein the metal oxide includes vanadium oxide and oxides of one or more elements selected from the group consisting of tin, molybdenum, tungsten and bismuth.

(4) The catalyst for oxidation of 2,2,2-trifluoroethanol according to any one of (1) to (3) above, wherein the metal oxide includes vanadium oxide and tin oxide.

(5) A process for producing trifluoroacetaldehyde and/or a trifluoroacetaldehyde hydrate, comprising oxidizing 2,2,2-trifluoroethanol with molecular oxygen or a molecular oxygen-containing gas in a gas-phase oxidation process carried out in the presence of the catalyst according to any one of (1) to (4) above.

(6) The process for producing trifluoroacetaldehyde and/or a trifluoroacetaldehyde hydrate according to (5) above, wherein the gas-phase oxidation process is carried out at a temperature of 200 to 400° C.

EFFECTS OF THE INVENTION

According to the present invention, there is provided a catalyst that has a long life and can oxidize 2,2,2-trifluoroethanol to produce, at high conversion and high selectivity, trifluoroacetaldehyde and/or a trifluoroacetaldehyde hydrate, a useful intermediate to make various pharmaceutical and agrochemical products. There is also provided a process for effectively producing trifluoroacetaldehyde and/or a trifluoroacetaldehyde hydrate using the catalyst.

Best Mode for Carrying Out the Invention

The present invention concerns a catalyst that oxidizes trifluoroethanol in the gas phase to produce trifluoroacetaldehyde and/or a trifluoroacetaldehyde hydrate, as well as a process for producing trifluoroacetaldehyde and/or a trifluoroacetaldehyde hydrate using the catalyst.

As shown by the chemical equation below, one molecule of water is produced during the oxidization reaction according to the present invention. Since trifluoroacetaldehyde 2 readily forms a hydrate 3, the product of the reaction may be obtained as either 1) trifluoroacetaldehyde, 2) trifluoroacetaldehyde hydrate, or 3) a mixture of trifluoroacetaldehyde and trifluoroacetaldehyde hydrate, depending on the conditions of the reaction.

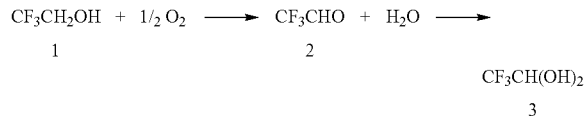

The catalyst of the present invention is composed of one or more metal oxides, including vanadium oxide, and zirconia as a carrier. The use of zirconia as a carrier not only enables the production of trifluoroacetaldehyde and/or a trifluoroacetaldehyde hydrate at high conversion and high selectivity, but also ensures long catalyst life.

The zirconia carrier of the present invention may form any type of crystal system, including monoclinic system, isometric system, trigonal system and amorphous.

The zirconia for use in the present invention preferably has a specific surface area in the range of 10 to 200 m$^2$/g. The zirconia with a specific surface area of less than 10 m$^2$/g has insufficient catalytic activity, whereas the zirconia with a 200 m$^2$/g or greater specific surface area leads to an increased combustion reaction and, thus, to a decrease in the selectivity.

The carrier may be provided in any shape, including spheres, cylinders, rings and semi-rings.

Vanadium oxide, the major component of the catalyst of the present invention, has a valency of a 4 or 5 and has a composition represented by $V_mO_n$ (where n/m=2 to 2.5). The amount of vanadium oxide relative to zirconia carrier (as determined for $V_2O_5$) is preferably in the range of 1 to 30 wt %, and more preferably in the range of 1 to 20 wt %. If the amount of vanadium oxide is less than 1 wt %, the conversion of the reaction becomes insufficient. If the amount of vanadium oxide is greater than 30 wt %, the selectivity of the reaction is decreased.

The source of vanadium for use in the present invention may be a vanadium oxide, such as vanadium pentoxide, a vanadium salt, such as vanadium chloride and vanadium acetyl acetonate, a vanadic acid salt, such as ammonium methavanadate, and vanadyl salts, such as vanadyl acetylacetonate, vanadyl oxalate and vanadyl sulfate.

The catalyst of the present invention may be a multi-component catalyst composed of a vanadium oxide and other metal oxides. The presence of other metal oxides provides advantageous effects such as increased catalytic activity and increased selectivity. Examples of metal elements present in the metal oxides for use in the present invention include tin, molybdenum, tungsten, bismuth, antimony, iron, nickel, chromium, manganese, cobalt and cerium. Of these elements, tin, molybdenum, tungsten and bismuth are preferred. Tin is particularly preferred in terms of the activity and the selectivity of the resulting catalyst.

The amount of the metal oxide in the catalyst is such that the molar ratio of the metal oxide to vanadium is in the range of 0.1 to 10.

The source of metals present in the metal oxides for use in the present invention may be a chloride, such as molybdenum (V) chloride, tungsten (VI) chloride, tin (IV) chloride, bismuth (III) chloride, antimony (III) chloride, iron (III) chloride, nickel (II) chloride, chromium (III) chloride, manganese (II) chloride, cobalt (II) chloride and cerium (III) chloride, a nitrate, such as bismuth (III) nitrate, iron (III) nitrate, nickel (II) nitrate, chromium (III) nitrate, cobalt (II) nitrate and cerium (III) nitrate, a sulfate, such as bismuth (III) sulfate, iron (III) sulfate and nickel (II) sulfate, a carbonate, such as nickel (II) carbonate, an organic acid salt, such as tin (IV) acetate and nickel (II) acetate, an oxide, such as molybdenum (VI) oxide, tungsten (IV) oxide and tin (IV) oxide, a molybdate, such as ammoniummolybdate, and a tungstate, such as ammonium tungstate.

The catalyst for use in the present invention can be prepared, for example, by heating/concentrating an aqueous solution or suspension of the catalyst components (concentration technique), or by impregnating the carrier with an aqueous solution of the catalyst components (impregnation technique). Alternatively, the catalyst components may be reduced and dissolved in the presence of oxalic acid or sulfite gas. In each process, the catalyst carrier combined with the catalyst components is dried at 100 to 200° C. and is then baked at 400 to 600° C. under a stream of a molecular oxygen-containing gas.

The reaction of the present invention is now described. The reactor for carrying out the reaction of the present invention may be any suitable reactor, including fixed-bed flow reactors and fluidized bed reactors. In using a fixed-bed flow reactor, 2,2,2-trifluoroethanol, along with molecular oxygen or a molecular oxygen-containing gas, is introduced into a reaction tube containing the catalyst and heated to a certain temperature.

The reaction temperature is preferably in the range of 200 to 400° C., and more preferably in the range of 250 to 350° C. If the reaction temperature is below 200° C., then the conversion becomes too low to ensure productivity. On the other hand, if the reaction temperature is above 400° C., then the combustion and other undesired side reactions take place, thus resulting in a decreased selectivity.

While the gaseous mixture may be passed at any suitable space velocity (SV), it is preferably passed at an SV in the range of 100 to 10000 hr$^{-1}$, and more preferably at an SV in the range of 1000 to 5000 hr$^{-1}$.

While 2,2,2-trifluoroethanol may be provided at any suitable concentration (v/v %), it is preferably provided at a concentration below the lower explosion limit of the compound in view of safety reason: It is typically provided at a concentration of 0.5 to 6 v/v %. It is preferred that the molar ratio of oxygen to 2,2,2-trifluoroethanol in the gaseous mixture is in the range of 1 to 20.

The molecular oxygen-containing gas for use in the present invention may be obtained by diluting oxygen with nitrogen, helium or other inert gases to a predetermined oxygen concentration. Air or air diluted with nitrogen is readily available and inexpensive and is thus preferably used.

The reaction gas may be either condensed by cooling or dissolved in water to forma n aqueous solution of trifluoroacetaldehyde hydrate. The solution is then distilled by known techniques to collect the desired trifluoroacetaldehyde and/or a trifluoroacetaldehyde hydrate.

EXAMPLES

The present invention will now be described with reference to examples, which are not intended to limit the scope of the invention in any way.

Example 1

Preparation of Catalyst

To a four-necked flask, 250 ml distilled water, 5.3 g ammonium methavanadate and 8.0 g ammonium molybdate were added and the mixture was heated to 80° C. to dissolve the materials. To this solution, 54 g of zirconia (cylindrical particles with a 3 mm diameter and a surface area of 53 $m^2/g$) were added and the mixture was concentrated and dried. Subsequently, the product was further dried at 200° C. for 1 hour. 20 ml of the resulting catalyst was packed in a 15 mm×600 mm stainless reaction tube. While air was passed through the reaction tube at a rate of 0.5 L/min, the tube was heated to 500° C. and baked for 3 hours.

The Reaction

A gas collector containing 600 g water was attached to the outlet of the reaction tube. Air and 2,2,2-trifluoroethanol were fed to the reaction tube at rates of 1.4 L/min and at 0.13 g/min, respectively, with the catalyst layer maintained at 260° C.

After 6 hours, the liquid in the gas collector was analyzed by $^{19}$F-NMR. The results indicated that 64% of 2,2,2-trifluoroethanol was converted and trifluoroacetaldehyde hydrate was obtained at a selectivity of 91%.

The reaction was further continued for 300 hours. The results of the same analysis revealed that no significant decrease was observed in the conversion of 2,2,2-trifluoroethanol or the selectivity of trifluoroacetaldehyde hydrate: 63% of 2,2,2-trifluoroethanol was converted and trifluoroacetaldehyde hydrate was obtained at a selectivity of 91%.

Example 2

Preparation of Catalyst

To a four-necked flask, 15 ml distilled water, 5.3 g ammonium methavanadate and 8.1 g oxalic acid were added and the mixture was stirred for 30 min to dissolve the materials. To this solution, 6.8 g of tin oxide (fine powder) was added and the mixture was stirred for additional 30 min. Subsequently, 54 g of zirconia (cylindrical particles with a 3 mm diameter and a surface area of 53 $m^2/g$) was added and the mixture was concentrated and dried by heating while stirred. The product was further dried at 200° C. for 1 hour. 20 ml of the resulting catalyst was packed in a 15 mm×600 mm stainless reaction tube. While air was passed through the reaction tube at a rate of 0.5 L/min, the tube was heated to 500° C. and baked for 3 hours.

The Reaction

The oxidation of 2,2,2-trifluoroethanol was carried out in the same manner as in Example 1, except that the temperature of the catalyst layer was 290° C.

After 6 hours of the reaction, the liquid in the gas collector was analyzed by $^{19}$F-NMR. The results indicated that 94% of 2,2,2-trifluoroethanol was converted and trifluoroacetaldehyde hydrate was obtained at a selectivity of 81%.

The reaction was further continued for 2000 hours. The results of the same analysis revealed that no significant decrease was observed in the conversion of 2,2,2-trifluoroethanol or the selectivity of trifluoroacetaldehyde hydrate: 93% of 2,2,2-trifluoroethanol was converted and trifluoroacetaldehyde hydrate was obtained at a selectivity of 82%.

Example 3

A catalyst was prepared in the same manner as in Example 1, except that ammonium molybdate was not used. The catalyst was used to oxidize 2,2,2-trifluoroethanol.

After 6 hours of the reaction, the liquid in the gas collector was analyzed by $^{19}$F-NMR. The results indicated that 67% of 2,2,2-trifluoroethanol was converted and trifluoroacetaldehyde hydrate was obtained at a selectivity of 83%.

The reaction was further continued for 300 hours. The results of the same analysis revealed that no significant decrease was observed in the conversion of 2,2,2-trifluoroethanol or the selectivity of trifluoroacetaldehyde hydrate: 67% of 2,2,2-trifluoroethanol was converted and trifluoroacetaldehyde hydrate was obtained at a selectivity of 82%.

Example 4

A catalyst was prepared in the same manner as in Example 1, except that zirconia having a specific surface area of 95 $m^2/g$ (cylindrical particles with a 3 mm diameter) was used and ammonium molybdate was not used. The catalyst was used to oxidize 2,2,2-trifluoroethanol. After 6 hours of the reaction, the liquid in the gas collector was analyzed by $^{19}$F-NMR. The results indicated that 62% of 2,2,2-trifluoroethanol was converted and trifluoroacetaldehyde hydrate was obtained at a selectivity of 82%.

The reaction was further continued for 300 hours. The results of the same analysis revealed that no significant decrease was observed in the conversion of 2,2,2-trifluoroethanol or the selectivity of trifluoroacetaldehyde hydrate: 61% of 2,2,2-trifluoroethanol was converted and trifluoroacetaldehyde hydrate was obtained at a selectivity of 83%.

Example 5

A catalyst was prepared in the same manner as in Example 1, except that zirconia having a specific surface area of 258 $m^2/g$ (spherical particles with a 3 mm diameter) was used and ammonium molybdate was not used. The catalyst was used to oxidize 2,2,2-trifluoroethanol. After 6 hours of the reaction, the liquid in the gas collector was analyzed by $^{19}$F-NMR. The results indicated that 68% of 2,2,2-trifluoroethanol was converted and trifluoroacetaldehyde hydrate was obtained at a selectivity of 69%.

The reaction was further continued for 100 hours. The results of the same analysis revealed that no significant decrease was observed in the conversion of 2,2,2-trifluoroethanol or the selectivity of trifluoroacetaldehyde hydrate: 66% of 2,2,2-trifluoroethanol was converted and trifluoroacetaldehyde hydrate was obtained at a selectivity of 67%.

Example 6

A catalyst was prepared in the same manner as in Example 1, except that ammonium molybdate was replaced by 4.9 g of ammonium tungstate. The catalyst was used to oxidize 2,2,2-trifluoroethanol. After 6 hours of the reaction, the liquid in the gas collector was analyzed by $^{19}$F-NMR. The results indicated that 72% of 2,2,2-trifluoroethanol was converted and trifluoroacetaldehyde hydrate was obtained at a selectivity of 80%.

The reaction was further continued for 100 hours. The results of the same analysis revealed that no significant decrease was observed in the conversion of 2,2,2-trifluoroethanol or the selectivity of trifluoroacetaldehyde hydrate: 71% of 2,2,2-trifluoroethanol was converted and trifluoroacetaldehyde hydrate was obtained at a selectivity of 81%.

Example 7

A catalyst was prepared in the same manner as in Example 1, except that ammoniummolybdate was replaced by 18 g of bismuth nitrate. The catalyst was used to oxidize 2,2,2-trifluoroethanol.

After 6 hours of the reaction, the liquid in the gas collector was analyzed by $^{19}$F-NMR. The results indicated that 70% of 2,2,2-trifluoroethanol was converted and trifluoroacetaldehyde hydrate was obtained at a selectivity of 79%.

The reaction was further continued for 100 hours. The results of the same analysis revealed that no significant decrease was observed in the conversion of 2,2,2-trifluoroethanol or the selectivity of trifluoroacetaldehyde hydrate: 70% of 2,2,2-trifluoroethanol was converted and trifluoroacetaldehyde hydrate was obtained at a selectivity of 80%.

Example 8

A catalyst was obtained in the same manner as in Example 1. The reaction was carried out in the same manner as in Example 1, except that 16 ml of the catalyst was used. After 6 hours of the reaction, the liquid in the gas collector was analyzed by $^{19}$F-NMR. The results indicated that 47% of 2,2,2-trifluoroethanol was converted and trifluoroacetaldehyde hydrate was obtained at a selectivity of 93%.

The reaction was further continued for 100 hours. The results of the same analysis revealed that no significant decrease was observed in the conversion of 2,2,2-trifluoroethanol or the selectivity of trifluoroacetaldehyde hydrate: 48% of 2,2,2-trifluoroethanol was converted and trifluoroacetaldehyde hydrate was obtained at a selectivity of 93%.

Example 9

A catalyst was obtained in the same manner as in Example 1. The reaction was carried out in the same manner as in Example 1, except that the temperature of the catalyst layer was 410° C. After 6 hours of the reaction, the liquid in the gas collector was analyzed by $^{19}$F-NMR. The results indicated that 95% of 2,2,2-trifluoroethanol was converted and trifluoroacetaldehyde hydrate was obtained at a selectivity of 69%. The reaction was further continued for 100 hours. The results of the same analysis revealed that no significant decrease was observed in the conversion of 2,2,2-trifluoroethanol or the selectivity of trifluoroacetaldehyde hydrate: 94% of 2,2,2-trifluoroethanol was converted and trifluoroacetaldehyde hydrate was obtained at a selectivity of 69%.

Comparative Example 1

A catalyst was prepared in the same manner as in Example 2, except that γ-alumina (spherical particles having a 2-4 mm diameter and a surface area of 140 m$^2$/g) was used as a carrier. The catalyst was used to oxidize 2,2,2-trifluoroethanol.

After 6 hours of the reaction, the liquid in the gas collector was analyzed by $^{19}$F-NMR. The results indicated that 88% of 2,2,2-trifluoroethanol was converted and trifluoroacetaldehyde hydrate was obtained at a selectivity of 88%.

The reaction was further continued for 72 hours. The results of the same analysis revealed that the catalytic activity was significantly decreased, as was the selectivity for trifluoroacetaldehyde hydrate: The conversion of 2,2,2-trifluoroethanol was 55% and the selectivity for trifluoroacetaldehyde hydrate was 70%.

Comparative Example 2

A catalyst was prepared in the same manner as in Example 1, except that silica (spherical particles having a 3 m diameter and a surface area of 80 m$^2$/g) was used as a carrier and ammoniummolybdate was not used. The catalyst was used to oxidize 2,2,2-trifluoroethanol.

After 6 hours of the reaction, the liquid in the gas collector was analyzed by $^{19}$F-NMR. The results indicated that the conversion of 2,2,2-trifluoroethanol, as well as the selectivity for trifluoroacetaldehyde hydrate, was impractically low: The conversion of 2,2,2-trifluoroethanol was 12% and the selectivity for trifluoroacetaldehyde hydrate was 40%.

The reaction was further continued for 72 hours. The results of the same analysis revealed that the conversion of 2,2,2-trifluoroethanol was significantly decreased, as was the selectivity for trifluoroacetaldehyde hydrate: The conversion of 2,2,2-trifluoroethanol was 10% and the selectivity for trifluoroacetaldehyde hydrate was 35%.

Comparative Example 3

A catalyst was prepared in the same manner as in Example 1, except that the zirconia carrier was replaced by α-alumina (spherical particles having a 3 mm diameter and a surface area of 3 m$^2$/g) and ammonium molybdate was not used. The catalyst was used to oxidize 2,2,2-trifluoroethanol. After 6 hours of the reaction, the liquid in the gas collector was analyzed by $^{19}$F-NMR. The results indicated that the catalyst did not have sufficient catalytic activity: only 24% of 2,2,2-trifluoroethanol was converted and trifluoroacetaldehyde hydrate was obtained at a selectivity of 85%.

The reaction was further continued for 72 hours. The results of the same analysis revealed that the catalytic activity was significantly decreased, as was the selectivity for trifluoroacetaldehyde hydrate: The conversion of 2,2,2-trifluoroethanol was 15% and the selectivity for trifluoroacetaldehyde hydrate was 68%.

Comparative Example 4

A catalyst was prepared in the same manner as in Example 1, except that the zirconia carrier was replaced by titania (spherical particles having a 3 mm diameter and a surface area of 69 m²/g) and ammonium molybdate was not used. The catalyst was used to oxidize 2,2,2-trifluoroethanol. After 6 hours of the reaction, the liquid in the gas collector was analyzed by $^{19}$F-NMR. The results indicated that the selectivity for trifluoroacetaldehyde hydrate was impractically low: While 93% of 2,2,2-trifluoroethanol was converted, trifluoroacetaldehyde hydrate was obtained at a low selectivity of 40%.

The reaction was further continued for 100 hours. The results of the same analysis revealed that the catalytic activity was significantly decreased, as was the selectivity for trifluoroacetaldehyde hydrate: The conversion of 2,2,2-trifluoroethanol was 80% and the selectivity for trifluoroacetaldehyde hydrate was 36%.

INDUSTRIAL APPLICABILITY

The catalyst of the present invention has a long life and can oxidize 2,2,2-trifluoroethanol to trifluoroacetaldehyde and/or a trifluoroacetaldehyde hydrate at high conversion and at high selectivity. Trifluoroacetaldehyde and trifluoroacetaldehyde hydrates, the products of the present invention, are useful intermediates to make various pharmaceutical and agrochemical products.

The invention claimed is:

1. A process for producing trifluoroacetaldehyde and/or a trifluoroacetaldehyde hydrate, comprising oxidizing 2,2,2-trifluoroethanol with molecular oxygen or a molecular oxygen-containing gas in a gas-phase oxidation process carried out in the presence of a catalyst comprising one or more metal oxides, including at least vanadium oxide and zirconia as a carrier.

2. The process for producing trifluoroacetaldehyde and/or a trifluoroacetaldehyde hydrate according to claim 1, wherein the gas-phase contact oxidation process is carried out at a temperature of 200 to 400° C.

3. The process for producing trifluoroacetaldehyde and/or a trifluoroacetaldehyde hydrate according to claim 1, wherein the zirconia has a specific surface area in the range of 10-200 m²/g.

4. The process for producing trifluoroacetaldehyde and/or a trifluoroacetaldehyde hydrate according to claim 1, wherein the metal oxide further includes an oxide of one or more elements selected from the group consisting of tin, molybdenum, tungsten and bismuth.

5. The process for producing trifluoroacetaldehyde and/or a trifluoroacetaldehyde hydrate according to claim 1, wherein the metal oxide further includes tin oxide.

6. A process for producing trifluoroacetaldehyde and/or a trifluoroacetaldehyde hydrate, comprising oxidizing 2,2,2-trifluoroethanol with molecular oxygen or a molecular oxygen-containing gas in a gas-phase oxidation process carried out in the presence of a catalyst comprising one or more metal oxides, including at least vanadium oxide and tin oxide, and zirconia as a carrier, wherein the gas phase oxidation process is carried out at a temperature of 200 to 400° C., and further wherein the zirconia has a specific surface area in the range of 10-200 m²/g.

* * * * *